United States Patent [19]

Munro et al.

[11] Patent Number: 5,707,995
[45] Date of Patent: Jan. 13, 1998

[54] PESTICIDAL PYRIMIDINE COMPOUNDS

[75] Inventors: David Munro, Maidstone; Royston Davis, Sittingbourne; Janet Anne Day, Faversham; Jacqueline Anne Wilkin, Maidstone, all of United Kingdom; William W. Wood, Trenton, N.J.

[73] Assignee: American Cyanamid Company, Parsippany, N.J.

[21] Appl. No.: 351,477

[22] PCT Filed: Jul. 15, 1993

[86] PCT No.: PCT/EP93/01880

§ 371 Date: Jul. 24, 1995

§ 102(e) Date: Jul. 24, 1995

[87] PCT Pub. No.: WO94/02470

PCT Pub. Date: Feb. 3, 1994

[30] Foreign Application Priority Data

Jul. 17, 1992 [EP] European Pat. Off. ............. 92306600

[51] Int. Cl.$^6$ ................... C07D 239/46; C07D 239/52; A01N 43/54

[52] U.S. Cl. .................. 514/256; 514/269; 514/274; 544/299; 544/301; 544/302; 544/303; 544/306; 544/311; 544/312; 544/313; 544/314; 544/319; 544/326; 544/327; 544/328; 544/329; 544/334; 544/335; 544/242

[58] Field of Search ................ 514/256, 269, 514/274; 544/299, 301, 302, 303, 306, 311, 312, 313, 314, 319, 326, 327, 328, 329, 334, 335, 242

[56] References Cited

U.S. PATENT DOCUMENTS 5,145,856 9/1992 Clough et al. ................ 514/274

FOREIGN PATENT DOCUMENTS 382375 8/1990 European Pat. Off. .

OTHER PUBLICATIONS

Chemical Abstracts 112:612g, vol. 112, 1990; Vainilavichius et al.

Shephard, Chemical Abstracts, vol. 72, entry 99507 (1970).

Netherlands Patent 6 81 4057 Derwent Abstract Aug. 31, 1993.

Primary Examiner—John M. Ford
Attorney, Agent, or Firm—Gregory M. Hill

[57] ABSTRACT

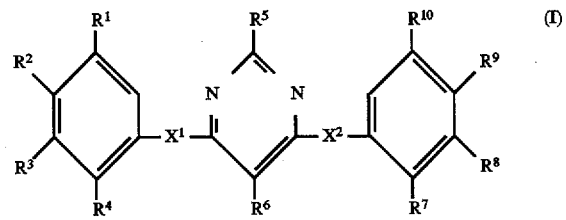

Compounds of formula (I) in which $X^1$ and $X^2$ each represents oxygen; $S(O)_n$, n being 0, 1 or 2; or CO, $CH_2$ or NR, R being hydrogen or alkyl; $R^1$ and $R^{10}$ are each hydrogen or halogen; $R^2$ and $R^9$ are each hydrogen, halogen, cyano, nitro, alkyl, halo-alkyl, alkoxy, alkylthio, amino, mono- or di-alkylamino, alkoxyalkyl, haloalkoxyalkyl or alkoxycarbonyl; $R^3$ and $R^8$ are each hydrogen, chlorine, alkyl, haloalkyl, haloalkenyl, halo-alkynyl, haloalkoxy, haloalkoxycarbenyl, haloalkylthio, haloalkoxyalkyl, haloalkylsulphinyl, or haloalkylsulphonyl, nitro or cyano; $R^4$ and $R^7$ are each hydrogen, halogen, alkyl or alkoxy; $R^5$ is hydrogen, halogen, cyano, alkyl, haloalkyl, alkoxy, alkylthio, alkylsulphonyl or phenyl; and $R^6$ is hydrogen or, when $R^5$ is hydrogen, alkyl; provided that either each phenyl is unsubstituted or at least one of $R^3$ and $R^8$ is not hydrogen, have useful pesticidal activity.

20 Claims, No Drawings

PESTICIDAL PYRIMIDINE COMPOUNDS

This is a section 371 application of PCT/EP93/01880, filed Jul. 15, 1993.

The present invention relates to substituted pyrimidine compounds, their preparation and use as pesticides.

Dutch Patent Specification No. 6814057 discloses a wide range of substituted pyrimidines and their use as fungicides.

J. Indian Chem. Soc., 52(8), 1975, 774–775, and 53(9), 1976, 913–914 discloses a number of 2-amino-4,6-bis aryloxy and arylimino pyrimidines and suggests that they may have useful biological properties.

It has now been found that a group of substituted pyrimidines generically described in NL-6814057 but not specifically disclosed therein have acaricidal activity which is significantly greater than that of 2-amino-substituted analogues.

The present invention provides a compound of the general formula

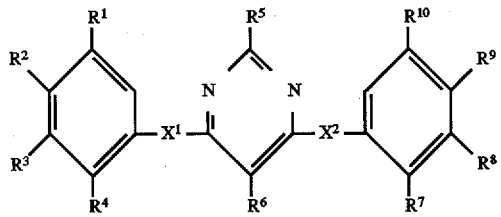

in which $X^1$ and $X^2$ are the same and each represents an oxygen atom; a group $S(O)_n$ in which n is 0, 1 or 2; or a group $CO$, $CH_2$ or $NR$ in which R represents a hydrogen atom or an alkyl group;

$R^1$ and $R^{10}$ are the same or different and each represents a hydrogen atom or a halogen atom;

$R^2$ and $R^9$ are the same or different and each represents a hydrogen atom, a halogen atom or a cyano, nitro, alkyl, haloalkyl, alkoxy, alkylthio, amino, mono- or di-alkylamino, alkoxyalkyl, haloalkoxyalkyl or alkoxycarbonyl group;

$R^3$ and $R^8$ are the same or different and each represents a hydrogen atom, a chlorine atom, or an alkyl, haloalkyl, haloalkenyl, haloalkynyl, haloalkoxy, haloalkoxycarbonyl, haloalkylthio, haloalkoxyalkyl, haloalkylsulphinyl, haloalkylsulphonyl, nitro or cyano group;

$R^4$ and $R^7$ are the same or different and each represents a hydrogen atom, a halogen atom or an alkyl or alkoxy group;

$R^5$ represents a hydrogen atom, a halogen atom, or a cyano, alkyl, haloalkyl, alkoxy, alkylthio, alkylsulphinyl or phenyl group; and $R^6$ represents a hydrogen atom or, when $R^5$ is hydrogen, an alkyl group;

provided that either each of the two phenyl rings is unsubstituted or at least one of $R^3$ and $R^8$ is other than hydrogen.

To maintain activity the phenyl rings of formula I must be either unsubstituted or at least one must be 3-substituted.

An alkyl group, unless otherwise specified, is suitably a straight chain or branched chain group containing up to 12 carbon atoms, for example up to 8 carbon atoms. Preferably an alkyl group contains up to 6 carbon atoms. Especially preferred alkyl groups are methyl, ethyl and butyl. Any alkyl moiety which forms part of another group, for example the alkyl of a haloalkyl group or each alkyl of an alkoxyalkyl group, suitably has up to 6 carbon atoms, preferably up to 4 carbon atoms. Preferred alkyl moieties are methyl and ethyl.

Halogen is fluorine, chlorine, bromine or iodine. Haloalkyl and haloalkoxy are especially trifluoromethyl, pentafluoroethyl, and trifluoromethoxy.

Preferably each of $X^1$ and $X^2$ represents an oxygen atom, a sulphur atom or an NH group; especially each of $X^1$ and $X^2$ represents an oxygen atom.

$R^1$ and $R^{10}$ are preferably the same and each represents a hydrogen or fluorine atom, especially a hydrogen atom.

$R^2$ and $R^9$ are preferably the same or different and each represents a hydrogen atom, a halogen atom, especially fluorine, chlorine or bromine, a nitro, alkyl or cyano group.

$R^3$ and $R^8$ are preferably the same or different, each representing a hydrogen, fluorine or chlorine atom, or a nitro, $C_{1-4}$alkyl, halo$C_{1-4}$alkyl, halo-$C_{1-4}$alkoxy, halo$C_{2-4}$alkenyl or ($C_{1-4}$alkoxy)carbonyl group. In especially preferred compounds each of $R^3$ and $R^8$ represents a hydrogen or chlorine atom or a trifluoromethyl, trifluoromethoxy, pentafluoroethyl or difluoroethenyl group or one of $R^3$ and $R^8$ represents a trifluoromethyl group and the other represents a hydrogen, chlorine or fluorine atom or a methyl, butyl, nitro, cyano or methoxycarbonyl group.

$R^4$ and $R^7$ are preferably the same or different and each represents a hydrogen or halogen atom or a $C_{1-4}$ alkyl group.

The pyrimidine ring, apart from the substituents at the 4- and the 6-positions, may carry one other substituent. $R^5$, in the 2-position, preferably represents a hydrogen or halogen atom or a halo $C_{1-4}$alkyl, $C_{1-4}$alkylthio, $C_{1-4}$alkylsulphinyl or phenyl group, especially a hydrogen, fluorine, chlorine or bromine atom or a methylthio or ethylthio group. $R^6$, in the 5-position, preferably represents a hydrogen atom or, when $R^5$ is hydrogen, a methyl group; $R^6$ is, however, especially hydrogen.

The compounds of formula I may be prepared by appropriate adaptation of conventional methods for obtaining disubstituted pyrimidines.

Conveniently, the compounds of formula I may be prepared by coupling appropriately substituted phenol(s), thiophenol(s) or aniline(s) and 4,6-dihalopyrimidines in basic conditions, optionally using a solvent, at ambient or, if necessary, at elevated temperatures, for example in the range of from 50° to 150° C. Desirably the reaction is carried out under nitrogen. Such procedures are well known and are described in, for example, J. Indian Chem. Soc. 52(8), 1975, 774–775, and 53(9), 1976, 913–914.

Naturally for the preparation of symmetrically substituted pyrimidine compounds of formula I, the reaction can be carried out in one step by using a molar ratio of pyrimidine to phenyl compound of at least 1:2. For unsymmetrical compounds, separate introduction of the two aryl substituents is required by a two-stage process.

The basic conditions may be provided using an alkali metal salt, conveniently a sodium or potassium salt, e.g. an alkali metal hydride or carbonate, such as sodium hydride or potassium carbonate or other conventional bases such as n-butyllithium. The solvent, if used, may be any polar organic solvent and must be selected to be compatible with the base utilised in the reaction. Thus with potassium carbonate, dimethylformamide or dimethylsulphoxide are both suitable, and with sodium hydride, tetrahydrofuran may be used.

It is also possible to generate a 2-substituted 4,6-disubstituted pyrimidine from a corresponding compound with a different 2-substitution by standard procedures. Thus, for example, a 2-halo-4,6-disubstituted pyrimidine may be prepared from a corresponding 2-amino compound using an alkyl nitrite, for example tert-butylnitrite, and a suitable solvent, such as carbon tetrachloride; also a 2-hydroxy-4,6-disubstituted pyrimidine may be converted into a 2-halo-analogue under the action of a phosphoryl halide, for example phosphoryl chloride or phosphoryl bromide, at an elevated temperature conveniently in the range of from 100 to the boiling temperature of the reaction medium; a reaction temperature of 130° to 150° C. is very suitable for this type of reaction.

Furthermore, it is possible and, for some compounds of the invention, more convenient, to prepare certain compounds of formula I from other compounds of formula I by standard techniques. Thus, for example, the SO or $SO_2$ oxides of compounds in which $X^1$ and $X^2$ are each sulphur may be prepared by conventional oxidation techniques; the N-alkyl analogues of NH compounds may be prepared by standard alkylation procedures, e.g. using methyl iodide in triethylamine or with hydrogenation involving a palladium-carbon catalyst; and the 2-alkoxy compounds may be prepared from 2-chloro analogues using sodium alkoxide in methanol.

Therefore, the present invention further provides a process for the preparation of a compound of general formula I, which comprises a) to prepare symmetrical compounds in which $R^1=R^{10}$, $R^2=R^9$, $R^3=R^8$ and $R^4=R^7$ reacting under basic conditions a 4,6-dihalopyrimidine of the general formula

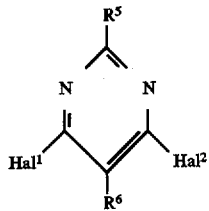

(II)

in which $R^5$ and $R^6$ are as defined above and each of $Hal^1$ and $Hal^2$, independently, represents a halogen atom preferably chlorine or bromine, with a compound of the general formula

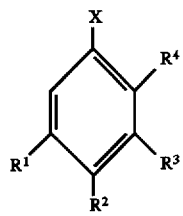

(III)

in which X represents a group $CH_2Hal$, COHal, OH, SH or NRH, Hal represents a halogen atom, suitably chlorine or bromine, and R, $R^1$, $R^2$, $R^3$ and $R^4$ are as defined above, in a molar ratio of at least 1:2;

b) to prepare unsymmetrical compounds in which $R^1$, $R^2$, $R^3$ and $R^4$ are not the same as $R^{10}$, $R^9$, $R^8$ and $R^7$ respectively, reacting under basic conditions a compound of formula II with a compound of formula III in a molar ratio of 1:1 and then reacting the resulting product with a compound of the general formula

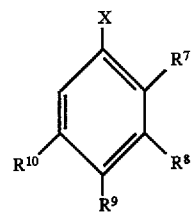

(IV)

in which X, $R^7$, $R^8$, $R^9$ and $R^{10}$ are as defined above, also in a molar ratio of 1:1; or c) converting a compound of the general formula

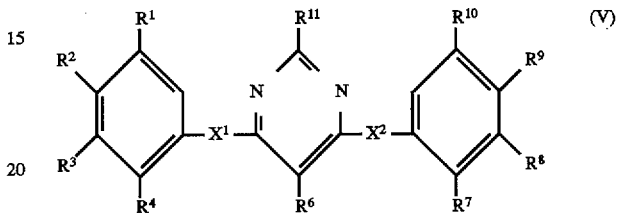

(V)

in which $X^1$, $X^2$, $R^1$, $R^2$, $R^3$, $R^4$, $R^6$, $R^7$, $R^8$, $R^9$ and $R^{10}$ are as defined above, and $R^{11}$ represents a group OH or $NH_2$, into a compound of general formula I, and, if desired or required, converting one compound of formula I into another compound of formula I.

The prepared compounds of formula I may, if desired, be isolated and purified using conventional techniques.

The compounds of formula II are either known or preparable by standard techniques, for example by the conversion of a corresponding pyrimidinol, (prepared following the Principal synthesis from the appropriate malonate and formamidine under reflux and in the presence of ethanol and sodium ethanolate) using a phosphoryl halide, e.g. chloride, in triethylamine at elevated temperature, for example at 100° C., as described in J. Org. Chem. 26, 1961, 4504.

Compounds of general formulae III and IV are either known or preparable by standard techniques, see for example J. Am. Chem. Soc. 73, 1951, 3470, which describes conditions suitable for the preparation of suitable phenols from the corresponding anilines using sodium nitrite and aqueous sulphuric acid at 0° C. followed by steam distillation.

Compounds of general formula V, and alkyl derivatives thereof, with the exception of 2-amino-4,6-bisphenoxypyrimidine which is disclosed in J. Indian Chem. Soc. 53(9), 1976, 913–914, and 2-amino-4,6-bis(3-chlorophenylimino)pyrimidine which is disclosed in J. Indian Chem. Soc. 52(8), 1975, 774–775, are believed to be novel and also form part of the present invention. They may be prepared by methods analogous to that for the preparation of the compounds of formula I. The 2-hydroxy-4,6-dihalopyrimidine precursor required for the preparation of compounds of formula V in which $R^{11}$ is hydroxy, may be prepared by procedures described in Helv. Chim. Acta, 72, 1989, 738, from 2,4,6-trihalopyrimidine reacted with dioxane in aqueous sodium hydroxide solution at ambient temperature. The other precursor compounds may also be prepared using standard literature procedures. The prime use of compounds of formula V is in the preparation of compounds of formula I, however one or two of the novel compounds of formula V unexpectedly possess pesticidal activity.

The compounds of the general formula I exhibit interesting and useful pesticidal, particularly acaricidal, activity and as such can be used to advantage to combat mites of the species Tetranychus and Panonychus. Moreover compounds of the present invention have been found to exhibit good activity against mite species which have developed resistance to existing commercial acaricides.

Certain compounds of the general formula I not only possess acaricidal activity but also exhibit useful activity against insect pests including whitefly and mosquito.

Furthermore, it has been found that compounds of the general formula I exhibit activity against animal ectoparasites, for example ticks on animals such as cattle, sheep, goats, pigs, dogs, horses, deer and cats.

The present invention therefore also provides a pesticidal composition comprising a carrier, preferably two carriers at least one of which is a surface-active agent, and, as active ingredient, a compound of general formula I. The invention additionally provides a method of combating pests, being primarily acarid pests, at a locus which comprises treating the locus with a compound or composition of the invention, and specifically provides the use as a pesticide, primarily as an acaricide, of a compound of general formula I. The dosage of active ingredient used may, for example, be from 5 to 500 ppm, preferably from 10 to 400 ppm, depending on the locus to be treated.

The present invention further provides a method of combating animal ectoparasites which comprises applying on to the skin or coat of an animal a compound of general formula I or a composition comprising such a compound as active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinires, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythrltol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other active ingredients, for example insecticides or fungicides, or, in appropriate circumstances, herbicides. The compounds of formula I may be found to be especially useful when applied in admixture with other insecticides and/or acaricides, e.g.

organophosphates, pyrethroids, carbamates, acyl ureas and organotin compounds, for example the commercial products azinphos-methyl, chlorpyriphos, phosalone, fenpropathin, bifenthrin, pirimicarb, triazamate, diflubenzuron, flufenoxuron, teflubenzuron and fenbutatin oxide. Other mixture partners which, with the compounds of the invention may yield useful control, are amitraz, hexythiazox, pyridaben, and fenpyroximate.

The following Examples illustrate the invention. Examples 1 and 2 illustrate the preparation of starting materials of formulae III and II respectively; Examples 3 to 6 illustrate the preparation of compounds of formula I.

EXAMPLE 1

Preparation of 4-bromo-3-trifluoromethylphenol

4-Bromo-3-trifluoromethylaniline (48 g, 0.2 mol) was treated with water (300 ml) and concentrated $H_2SO_4$ (36 ml) at 60° C. for 1 hour. The resulting suspension was cooled in an ice bath and treated with sodium nitrite (16 g, 0.23 mol) in water (30 ml) maintaining the temperature of the reaction mixture below 10° C. The resulting solution was stirred at 0° C. for 1 hour, and then added portionwise, over 1 hour, to a 25% $H_2SO_4$ aqueous solution (160 ml) whilst steam distilling. After collecting approximately 1 liter of distillate, the aqueous distillate was extracted with ether and the organic solution dried using $MgSO_4$, filtered and concentrated. The product, 4-bromo-3-trifluoromethylphenol, was obtained by distillation under reduced pressure. Yield 18.0 g (37%); boiling point 68–71/1 mmHg.

Elemental Analysis (%): Calculated: C 34.9 H 1.7
Found: C 34.9 H 1.7

EXAMPLE 2

Preparation of 4,6-dichloro-2-trifluoromethylpyrimidine

Sodium (13 g, 0.57 mol) was dissolved in ethanol (500 ml) and diethyl malonate (84 g, 0.53 mol) was added, followed by trifluoromethylformamidine (62 g, 0.55 mol). The mixture was heated under reflux for 12 hours. On cooling, the mixture was concentrated under reduced pressure, and the product was taken up in water. On acidification with concentrated HCl, the product precipitated and was collected. Yield: 27.5 g (28%).

The precipitate (5.0 g, 0.028 mol) was suspended in triethylamine (20 ml) and was treated carefully with $POCl_3$ (20 ml). After the exotherm had subsided, the reaction mixture was heated at 100° C. for 2 hours, and then cooled and poured onto ice. The product was extracted into diethyl ether, dried over $Na_2SO_4$ and concentrated under reduced pressure. The final product, 4,6-dichloro-2-trifluoromethylpyrimidine, was obtained by bulb-to-bulb distillation. Yield: 3.2 g (52%); boiling point: 120° C./20 mmHg.

EXAMPLE 3

Preparation of 4,6-bis(4-chloro-3-trifluoromethylphenoxy)pyrimidine

4-Chloro-3-trifluoromethylphenol (10.0 g, 0.051 mol) and 4,6-dichloropyrimidine (3.7 g, 0.025 mol) were heated to 60° C. in dimethylsulphoxide (75 ml) with potassium carbonate (10 g) under nitrogen for 12 hours. The mixture was then poured into water and the product extracted into diethyl ether. The organic layer was dried using $Na_2SO_4$, filtered and concentrated. The product, 4,6-bis(4-chloro-3-trifluoromethylphenoxy)pyrimidine, was obtained by column chromatography (eluting with 5:1, hexane:ethyl acetate) and recrystallization (diethyl ether/hexane). Yield 11.0 g (94%); melting point 111° C.

Elemental Analysis (%):
Calculated: C 46.1 H 1.7N 6.0
Found: C 47.3 H 1.8N 5.9

EXAMPLE 4

Preparation of 4,6-bis(3-trifluoromethylphenoxy)-2-bromo-pyrimidine a) Preparation of 4,6-bis(3-trifluoromethylphenoxy) pyrimidin-2-one Sodium hydroxide (20 g, 0.5 mol) in water (160 ml) was added to a solution of 2,4,6-tri-chloropyrimidine (36.7g, 0.2 mol) in dioxane (600 ml). The mixture was stirred for 4 hours to give a thick white precipitate. The mixture was concentrated in vacuo and the residue recrystallized from boiling water. Yield: 18 g (55%).

The residue, 4,6-dichloropyrimidin-2-one, (8.0 g, 0.049 mol) and 3-trifluoromethylphenol (20 g, 0.123 mol) were heated in dimethylformamide (250 ml) with potassium carbonate (16 g) under nitrogen at 100° C. for 12 hours. The mixture was then poured into water and the precipitate collected. The product, 4,6-bis(3-trifluoro-methylphenoxy) pyrimidin-2-one, was obtained by recrystallization from methanol/water and column chromatography (eluting with 1:1, hexane:ethyl acetate). Yield: 2.5 g (12%).

Elemental Analysis (%):
Calculated: C 44.6 H 1.7N 5.8
Found: C 45.7 H 2.1N 5.7 b) Preparation of 4,6-bis(3-trifluoromethylphenoxy)-2-bromo-pyrimidine 4,6-Bis(3-trifluoromethylphenoxy)-pyrimidin-2-one (4.0 g, 0.0096 mol) and $POBr_3$ (100g) were heated at 140° C. for 48 hours. The mixture was then poured onto a mixture of 2N NaOH (500 ml) and ice. The product was extracted into diethyl ether, dried using $Na_2SO_4$, filtered and concentrated under reduced pressure. The product was obtained by column chromatography (3:1, hexane: ethyl acetate) and recrystallization (ethyl acetate/hexane). Yield: 1.0 g (22%); melting point 126°–129° C.

Elemental Analysis (%):
Calculated: C 45.1 H1.9N5.9
Found: C 45.7 H2.1N6.1

EXAMPLE 5

Preparation of 4,6-bis<4-fluoro-3-trifluoromethylphenoxyl)-2-chloro-pyrimidine

2-Amino-4,6-bis(4-fluoro-3-trifluoromethylphenoxy) pyrimidine (3.0 g, 6.7 mmol) was dissolved in carbon tetrachloride (75 ml) and the resulting solution was treated with t-butylnitrite (1.2 ml, 13.4 mmol). The mixture was heated at 30° C. for 48 hours and then poured into water. The product was extracted in dichloromethane, dried over sodium sulphate, filtered and concentrated under reduced pressure. The product, 4,6-bis(4-fluoro-3-trifluoromethylphenoxy)-2-chloro-pyrimidine, was obtained as an oil by column chromatography (eluting with 5:1, hexane:ethyl acetate). Yield 0.3 g (10%); mass 471 ($M^+$+H); N.m.r: 7.3–7.5 (6H, m, aromatics), 6.35 (1H,s,H-5).

Elemental Analysis (%):
Calculated: C 49.6 H 1.9N 6.4
Found: C 49.8 H 2.1N 6.4

EXAMPLE 6

Preparation of 4-(4-cyanophenoxy)-6-<4-fluoro-3-trifluoromethyl-phenoxy)-pyrimidine a) Preparation of 4-fluoro-6-<4-fluoro-3-trifluoromethylphenoxy)pyrimidine 4,6-difluoropyrimidine (2.0 g, 0.017 mol) was placed in dimethylformamide (150 cm³) with potassium carbonate (2.5 g) and the temperature reduced to about −20° C. 4-fluoro-3-trifluoro-methylphenol (2.9 g in 25 cm³ of dimethylformamide) was then added dropwise over 2 hours. The mixture was then left to stir for 4 hours between −30° and −20° C. After this time gas chromatography showed the reaction to be incomplete, so the mixture was left in the freezer overnight to prevent it from reaching room temperature. The mixture was then left to stir for a further 5 hours at −20° C. after which time gas chromatography showed no further reaction. The mixture was then poured into water, the resultant solid filtered and recrystallised from cyclohexane. Yield 0.9 g (21%):
Calculated: C 47.8 H 1.8 N 10.1
Found: C 48.0 H 2.2 N 10.1
A further 0.5 g of product was recovered from the recrystallisation filtrate, to give a total yield of 31%.

b) Preparation of 4-(4-cyanophenoxy)-6-(4-fluoro-3-trifluoro-methylphenoxy)-pyrimidine 4-fluoro-6-(4-fluoro-3-trifluoromethylphenoxy)-pyrimidine (0.9 g, 3.3 mmol) was placed in dimethylformamide (100 cm³) with potassium carbonate (0.6 g) and the temperature reduced to 0° C. 4-cyanophenol (0.37 g in 20 cm³ dimethylformamide) was then added dropwise and the mixture left to stir whilst maintaining the temperature at <5° C. for 6 hours. After this time gas chromatography showed little or no reaction so a further 0.2 equivalent of 4-cyanophenol was added, and the mixture left to stir overnight with the temperature reaching room temperature. After this time, gas chromatography and thin layer chromatography showed the reaction to be complete, so the mixture was poured into 100 cm³ of water and the resultant solid filtered and recrystallised from cyclohexane. Yield 0.93 g (75%); melting point 131°–132° C.
Calculated: C 57.6 H 2.4 N 11.2
Found: C 57.5 H 2.6 N 11.2

EXAMPLES 7 TO 63

By methods analogous to those of Examples 3 to 6, further compounds of formula I were prepared. Details are given in Table I below, with reference to the following formula:

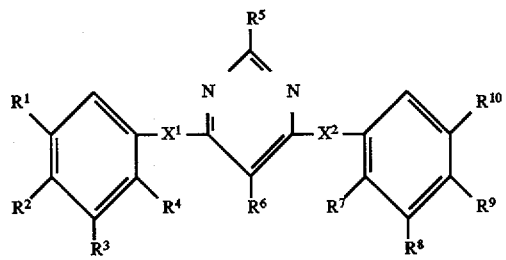

$R^4$ and $R^7$ are each hydrogen.

TABLE 1

| Ex. No. | $R^1$ | $R^2$ | $R^3$ | $X^1$ | $R^5$ | $R^6$ | $X^2$ | $R^8$ | $R^9$ | $R^{10}$ | Melting Point (°C.) | Elemental Analysis (% Calc./Found) C | H | N |
|---|---|---|---|---|---|---|---|---|---|---|---|---|---|---|
| 7 | H | H | $CF_3$ | O | H | H | O | $CF_3$ | H | H | 72.0 | 54.0 / 54.2 | 2.5 / 2.6 | 7.0 / 7.4 |
| 8 | H | H | $CF_3$ | S | H | H | S | $CF_3$ | H | H | 157.0 | 50.0 / 50.4 | 2.3 / 2.2 | 6.5 / 7.0 |
| 9 | H | H | $CF_3$ | NH | H | H | NH | $CF_3$ | H | H | 195.0 | 54.3 / 54.1 | 3.0 / 3.5 | 14.1 / 14.4 |
| 10 | H | H | $CF_3$ | O | H | $CH_3$ | O | $CF_3$ | H | H | 82.3 | 55.1 / 54.9 | 2.9 / 3.1 | 6.8 / 6.7 |
| 11 | H | H | $OCF_3$ | O | H | H | O | $OCF_3$ | H | H | oil | 50.0 / 51.0 | 2.3 / 2.6 | 6.5 / 6.6 |
| 12 | H | H | $CF_3$ | O | $SCH_3$ | H | O | $CF_3$ | H | H | 86.4 | 51.1 / 50.9 | 2.7 / 2.9 | 6.3 / 6.2 |
| 13 | H | H | $CF_3$ | O | $CH_3$ | H | O | $CF_3$ | H | H | 104.9 | 55.1 / 56.1 | 2.9 / 3.0 | 6.8 / 6.8 |
| 14 | H | H | $CF_3$ | O | $SC_2H_5$ | H | O | $CF_3$ | H | H | 48.7 | 52.2 / 52.1 | 3.0 / 3.2 | 6.1 / 6.1 |
| 15 | H | H | $CF_3$ | O | $SOC_2H_5$ | H | O | $CF_3$ | H | H | 82.9 | 50.4 / 50.4 | 2.9 / 3.2 | 5.9 / 5.8 |
| 16 | H | H | Cl | O | H | H | O | Cl | H | H | oil | 57.9 / 55.3 | 3.0 / 3.7 | 8.4 / 5.1 |
| 17 | H | H | $CF_3$ | O | H | H | O | H | H | H | 89.0 | 61.4 / 61.1 | 3.3 / 3.5 | 8.4 / 8.1 |
| 18 | H | $NO_2$ | $CF_3$ | O | H | H | O | $CF_3$ | $NO_2$ | H | 136.0 | 44.1 / 45.0 | 1.6 / 2.0 | 11.4 / 11.3 |
| 19 | H | H | $CF_3$ | O | H | H | O | F | H | H | 47.0 | 58.3 / 58.8 | 2.9 / 3.1 | 8.0 / 8.1 |
| 20 | H | H | $CF_3$ | O | H | H | O | Cl | H | H | 78.0 | 55.7 / 55.4 | 2.7 / 2.8 | 7.6 / 7.7 |
| 21 | H | H | $CF_3$ | O | H | H | O | $CH_3$ | H | H | 61.0 | 62.4 / 62.3 | 3.8 / 4.0 | 8.1 / 7.9 |
| 22 | H | H | $C_2F_5$ | O | H | H | O | $C_2F_5$ | H | H | oil | 48.0 / 48.4 | 2.0 / 2.3 | 5.6 / 5.7 |
| 23 | F | H | $CF_3$ | O | H | H | O | $CF_3$ | H | F | 70.0 | 49.5 | 1.8 | 6.4 |

TABLE 1-continued

| Ex. No. | R¹ | R² | R³ | X¹ | R⁵ | R⁶ | X² | R⁸ | R⁹ | R¹⁰ | Melting Point (°C.) | C | H | N |
|---|---|---|---|---|---|---|---|---|---|---|---|---|---|---|
| | | | | | | | | | | | | 51.5 | 1.9 | 6.3 |
| 24 | H | H | CF₃ | O | Cl | H | O | CF₃ | H | H | 108–111 | 49.7 | 2.1 | 6.4 |
| | | | | | | | | | | | | 50.1 | 2.1 | 6.5 |
| 25 | H | Br | CF₃ | O | H | H | O | CF₃ | Br | H | 119.3–121.4 | 38.7 | 1.5 | 5.0 |
| | | | | | | | | | | | | 38.9 | 1.8 | 5.1 |
| 26 | H | Cl | CF₃ | O | Cl | H | O | CF₃ | Cl | H | 135–136 | 42.9 | 1.4 | 5.6 |
| | | | | | | | | | | | | 43.4 | 1.6 | 5.5 |
| 27 | H | F | CF₃ | O | H | H | O | CF₃ | F | H | 200° C.*/0.6 mmHg | 49.6 | 1.8 | 6.4 |
| | | | | | | | | | | | | 49.9 | 2.4 | 5.6 |
| 28 | H | Cl | CF₃ | O | SCH₃ | H | O | CF₃ | Cl | H | 110.4–110.5 | 44.4 | 2.0 | 5.3 |
| | | | | | | | | | | | | 44.7 | 2.3 | 5.4 |
| 29 | H | CN | CF₃ | O | H | H | O | CF₃ | CN | H | 132.0–138.0 | 53.3 | 1.8 | 12.4 |
| | | | | | | | | | | | | 53.3 | 2.4 | 12.4 |
| 30 | H | H | H | O | H | H | O | H | H | H | 109.5 | 72.7 | 4.5 | 10.6 |
| | | | | | | | | | | | | 73.6 | 4.8 | 11.0 |
| 31 | H | H | H | O | SCH₃ | H | O | H | H | H | 109.6 | 65.8 | 4.5 | 9.0 |
| | | | | | | | | | | | | | 4.5 | 8.9 |
| 32 | H | Cl | CF₃ | O | CF₃ | H | O | CF₃ | Cl | H | 116–120 | 42.5 | 1.3 | 5.2 |
| | | | | | | | | | | | | 43.5 | 2.2 | 4.9 |
| 33 | H | Cl | CF₃ | O | F | H | O | CF₃ | Cl | H | 126.6–127.1 | 44.4 | 1.6 | 5.8 |
| | | | | | | | | | | | | 44.3 | 1.9 | 5.7 |
| 34 | H | H | CF₃ | O | C₆H₅ | H | O | CF₃ | H | H | 84.0–85.0 | 60.5 | 3.0 | 5.9 |
| | | | | | | | | | | | | 60.4 | 3.3 | 5.7 |
| 35 | H | NO₂ | H | O | H | H | O | CF₃ | H | H | 126.0–127.0 | 54.2 | 2.7 | 11.2 |
| | | | | | | | | | | | | 54.2 | 2.7 | 12.0 |
| 36 | H | F | H | O | H | H | O | CF₃ | H | H | 117.9–118.4 | 59.0 | 2.9 | 8.0 |
| | | | | | | | | | | | | 60.5 | 2.9 | 8.7 |
| 37 | H | F | CF₃ | O | SCH₃ | H | O | CF₃ | F | H | 97.0–98.0 | 47.3 | 2.1 | 5.8 |
| | | | | | | | | | | | | 48.0 | 2.6 | 6.0 |
| 38 | H | Cl | CF₃ | O | F | H | O | CF₃ | Cl | H | 129.0–130.0 | 44.4 | 1.4 | 5.7 |
| | | | | | | | | | | | | 44.3 | 1.7 | 5.7 |
| 39 | H | F | H | O | H | H | O | CF₃ | F | H | 122.0–123.0 | 56.0 | 2.2 | 7.6 |
| | | | | | | | | | | | | 57.3 | 2.9 | 7.7 |
| 40 | H | H | CF₃ | O | H | H | O | H | CN | H | 196.0–197.0 | 60.6 | 2.8 | 11.7 |
| | | | | | | | | | | | | 59.4 | 3.0 | 10.6 |
| 41 | H | CN | CF₃ | O | SCH₃ | H | O | CF₃ | CNH | H | 148.0–149.0 | 50.3 | 2.4 | 11.3 |
| | | | | | | | | | | | | 51.1 | 2.4 | 11.2 |
| 42 | H | F | CF₃ | O | C₆H₅ | H | O | CF₃ | F | H | 78.0–79.0 | 56.3 | 2.4 | 5.5 |
| | | | | | | | | | | | | 56.0 | 2.5 | 5.3 |
| 43 | H | H | C₂F₅ | O | SCH₃ | H | O | C₂F₅ | H | H | 61.0–62.0 | 46.1 | 2.2 | 5.1 |
| | | | | | | | | | | | | 46.1 | 2.4 | 5.1 |
| 44 | H | H | CH—CF₂ | O | H | H | O | CH—CF₂ | H | H | oil | — | | |
| 45 | H | F | CF₃ | O | H | H | O | CF₃ | H | H | 57.0–58.0 | 51.8 | 2.4 | 6.7 |
| | | | | | | | | | | | | 51.8 | 2.4 | 6.7 |
| 46 | H | F | CF₃ | O | H | H | O | H | NO₂ | H | oil | 51.7 | 2.3 | 10.6 |
| | | | | | | | | | | | | 51.5 | 2.5 | 10.5 |
| 47 | H | Br | CF₃ | O | Cl | H | O | CF₃ | Br | H | 192.0–193.0 | 36.5 | 1.2 | 4.7 |
| | | | | | | | | | | | | 36.3 | 1.5 | 4.7 |
| 48 | H | F | CF₃ | O | H | H | O | H | Cl | H | oil | 53.1 | 2.3 | 7.3 |
| | | | | | | | | | | | | 53.5 | 2.6 | 7.3 |
| 49 | H | F | CF₃ | O | H | H | O | Cl | H | H | 61.9–62.7 | 53.1 | 2.3 | 7.3 |
| | | | | | | | | | | | | 53.3 | 2.6 | 7.2 |
| 50 | H | F | CF₃ | O | H | H | O | F | H | H | oil | 55.4 | 2.4 | 7.6 |
| | | | | | | | | | | | | 55.6 | 2.6 | 7.6 |
| 51 | H | F | CF₃ | O | H | H | O | CH₃ | H | H | oil | 59.3 | 3.3 | 7.3 |
| | | | | | | | | | | | | 59.6 | 3.4 | 7.7 |
| 52 | H | H | C₂F₅ | O | Cl | H | O | C₂F₅ | H | H | 85.0–87.0 | 44.9 | 1.7 | 5.2 |
| | | | | | | | | | | | | 44.6 | 2.1 | 5.3 |
| 53 | H | F | CF₃ | O | H | H | O | CF₃ | Cl | H | 68.0 | 47.7 | 1.8 | 6.2 |
| | | | | | | | | | | | | 47.4 | 2.0 | 6.1 |
| 54 | H | F | CF₃ | O | H | H | O | C(CH₃)₃ | H | H | 69.7–71.6 | 62.1 | 4.4 | 6.9 |
| | | | | | | | | | | | | 62.9 | 4.8 | 6.9 |
| 55 | H | F | CF₃ | O | H | H | O | H | C(CH₃)₃ | H | 104.6–105.1 | 62.1 | 4.4 | 6.9 |
| | | | | | | | | | | | | 62.4 | 4.8 | 6.9 |
| 56 | H | F | CF₃ | O | H | H | O | NO₂ | H | H | 103.0–103.2 | 51.6 | 2.3 | 10.6 |
| | | | | | | | | | | | | 51.4 | 2.5 | 10.6 |
| 57 | H | H | CF₃ | O | H | H | O | CF₃ | Cl | H | oil | — | | |
| 58 | H | F | CF₃ | O | H | H | O | CN | H | H | 80.9–81.3 | 57.6 | 2.4 | 11.2 |
| | | | | | | | | | | | | 57.1 | 2.7 | 11.2 |
| 59 | H | F | CF₃ | O | H | H | O | CO₂CH₃ | H | H | 71.0–72.0 | 55.9 | 3.0 | 6.9 |
| | | | | | | | | | | | | 55.8 | 3.2 | 6.9 |
| 60 | H | F | CF₃ | O | SCH₃ | H | O | CF₃ | H | H | 86.5–87.2 | 49.0 | 2.4 | 6.0 |
| | | | | | | | | | | | | 48.7 | 2.7 | 6.3 |
| 61 | H | Br | CF₃ | O | H | H | O | CF₃ | H | H | oil | 45.1 | 2.0 | 5.8 |

TABLE 1-continued

| Ex. No. | R¹ | R² | R³ | X¹ | R⁵ | R⁶ | X² | R⁸ | R⁹ | R¹⁰ | Melting Point (°C.) | Elemental Analysis (% Calc./Found) C | H | N |
|---|---|---|---|---|---|---|---|---|---|---|---|---|---|---|
| 62 | H | Br | CF₃ | O | H | H | O | CF₃ | F | H | oil | 45.0 / 43.5 / 43.9 | 2.4 / 1.6 / 2.0 | 5.9 / 5.6 / 5.6 |
| 63 | H | F | CF₃ | O | Cl | H | O | CF₃ | H | H | 105.3–105.5 | 47.8 / 46.7 | 1.8 / 2.1 | 6.2 / 6.2 |

*boiling point

EXAMPLES 64 TO 67

By methods analogous to those of Examples 3 to 6, further compounds of formula I were prepared. Details are given in Table II below, with reference to the following formula:

TABLE II

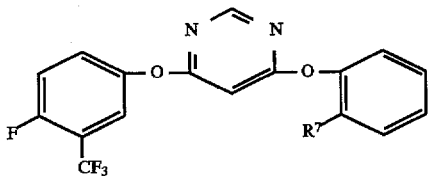

| Ex No. | R⁷ | Melting Point (°C.) | Elemental Analysis (% Calc./Found) C | H | N |
|---|---|---|---|---|---|
| 64 | Cl | oil | 53.1 / 53.2 | 2.3 / 2.9 | 7.3 / 6.9 |
| 65 | F | 73.0–73.1 | 55.4 / 55.7 | 2.4 / 2.7 | 7.6 / 7.5 |
| 66 | C(CH₃)₃ | oil | 52.1 / 52.7 | 4.4 / 4.8 | 6.9 / 6.6 |
| 67 | CH₃ | oil | 59.3 / 59.7 | 3.3 / 3.3 | 7.7 / 7.4 |

EXAMPLE 68

Acaricidal Activity

The acaricidal activity of the compounds of the invention was determined in the following tests employing the glasshouse red spider mite, *Tetranychus urticae* (T.u.).

In each test solutions or suspensions of test compound were made up over a range of concentrations in water (initially 0.1%w) containing 10%w acetone and 0.025% w "TRITON X-100" (trade mark) surface active agent (the condensation product of ethylene oxide with an alkyl phenol). These solutions were sprayed at a rate equivalent to 340 liters per hectare ($3.4 \times 10^{-5}$ m³/m²) onto petri dishes containing either test species per se or diet onto which test species were subsequently introduced, as indicated. The tests were all conducted under normal insectary conditions (23° C.±2° C., fluctuating humidity and 16 hours day length light).

The results of testing at the initial test concentrations were graded:

Grade A represents at least 70% mortality of the pest
Grade B represents from 40% to 69% mortality.

For compounds achieving Grade A at initial test concentration, mortality assessments were made as indicated below, in terms of percentage mortality figures. In each test a LC₅₀ (the dosage of active material required to kill half of the test species) for the compound was calculated from the mortality figures and compared with the corresponding LC₅₀ for a standard insecticide (either ethyl parathion or chlorfenson, as indicated) in the same test. The results are expressed as toxicity indices thus:

$$\text{toxicity index} = \frac{LC_{50} \text{ (standard insecticide)}}{LC_{50} \text{ (test compound)}} \times 100$$

a) Acaricidal activity—mite adults Tu

Acaricidal activity was assessed using adult glasshouse red spider mites, *Tetranychus urticae* (T.u.), 7–10 days after hatching, by the following procedure:

2 cm diameter discs cut from the leaves of French bean plants were placed on filter paper kept moist by a cotton wool wick dipped into water. Prior to testing, each leaf disc was infested with 10 adult mites. The mites and discs were then sprayed with solutions of the test compound made up as above, at a rate equivalent to 340 liters per hectare ($3.4 \times 10^5$ m³/m²). The mites were held under the normal insectary conditions. The numbers of dead and moribund adults were assessed after 48 hours and the percentage mortality calculated.

b) Acaricidal activity—ovicide TuOA

Acaricidal activity was assessed employing eggs of the glasshouse red spider mite, *Tetranychus urticae* (T.u.), less than 24 hours old, by the following procedure.

2 cm diameter leaf discs cut from the leaves of French bean plants were placed on filter paper, kept moist by a cotton wool wick dipped into water.

On the day before spraying, each leaf disc was infested with 10 female adult mites. On the day of the test, the adults were removed, leaving the eggs laid overnight on the discs. The leaf discs were then sprayed with solutions of test compound made up as above, at a rate equivalent to 340 liters per hectare ($3.4 \times 10^{-5}$ m³/m²).

Throughout the test, the eggs were held under the normal insectary conditions. After 7–10 days, the numbers of hatched nymphs and unhatched eggs were assessed and the percentage mortality calculated.

The LC₅₀ (the dosage of active material required to kill half of the test species) for each test compound was calculated from the mortality figure and compared with the corresponding LC₅₀ for a standard insecticide in the same test. For Tu ethyl parathion was used as the standard compound; for TuOA chlorfenson was used as the standard.

The results are given in Table III below.

TABLE III

Acaricidal Activity

| Compound of Example No. | Toxicity Index Tu | Tu OA |
|---|---|---|
| 3 | 320 | 720 |
| 4 | 67 | |
| 5 | 400 | 1400 |
| 6 | 12 | 140 |
| 7 | 75 | 94 |
| 8 | 5 | |
| 9 | <4 | <20 |
| 10 | | B |
| 11 | <3 | |
| 12 | 28 | 66 |
| 13 | 5 | |
| 14 | 23 | 63 |
| 15 | | <18 |
| 16 | 5 | 20 |
| 17 | | 41 |
| 18 | 70 | 34 |
| 19 | 10 | |
| 20 | 27 | 35 |
| 21 | 4 | 12 |
| 22 | 100 | 41 |
| 23 | 4 | |
| 24 | 170 | <16 |
| 25 | 98 | 180 |
| 26 | 150 | 180 |
| 27 | 360 | 2200 |
| 28 | 18 | B |
| 29 | 62 | 250 |
| 30 | | <23 |
| 31 | | <12 |
| 32 | 22 | 73 |
| 33 | 60 | 200 |
| 34 | 11 | <19 |
| 35 | 25 | <16 |
| 36 | 21 | 60 |
| 37 | 190 | 730 |
| 38 | 100 | |
| 39 | 42 | 390 |
| 40 | 35 | 87 |
| 41 | 10 | 94 |
| 42 | 36 | 20 |
| 43 | | 57 |
| 44 | | 36 |
| 45 | 110 | 640 |
| 46 | 73 | 100 |
| 47 | 18 | |
| 48 | 21 | 160 |
| 49 | 77 | 190 |
| 50 | 24 | 170 |
| 51 | 38 | 65 |
| 52 | 100 | 130 |
| 53 | 760 | 1500 |
| 54 | 29 | 81 |
| 55 | 11 | 62 |
| 56 | 128 | 700 |
| 57 | 94 | 870 |
| 58 | 72 | 650 |
| 59 | 6 | <4 |
| 60 | 65 | A |
| 61 | 57 | A |
| 62 | 130 | A |
| 63 | 120 | 760 |
| 64 | 2 | <27 |
| 65 | 10 | 50 |
| 66 | 11 | 57 |
| 67 | 19 | 100 |

EXAMPLE 69

Comparison Tests

The acaricidal activity of the prior art compound 2-amino-4,6-bisphenoxypyrimidine and of the 2-amino analogues of the substituted pyrimidines of Examples 3 and 7 was determined following the procedures of Example 68 above. The results are given in Table IV below, and for ease of comparison the data for the compounds of Examples 3 and 7 are also included in the Table.

TABLE IV

| Compound | Toxicity Index Tu | TuOA |
|---|---|---|
| Example 3 | 320 | 720 |
| Example 7 | 75 | 94 |
| Comparison A | C | C |
| Comparison B | C | C |
| Comparison C | C | C |

Comparison A is the 2-amino analogue of the compound of Example 3, and Comparison B is the 2-amino analogue of the compound of Example 7. Comparison C is 2-amino-4,6-bisphenoxy-pyrimidine. Grade C represents less than 40% mortality of the pest, whereas the Toxicity Index is only estimated when Grade A activity (i.e. at least 70% mortality) is achieved.

It can clearly be seen that the compounds of the present invention have a significantly greater acaricidal activity than the direct 2-amino analogues.

EXAMPLE 70

Insecticidal Activity

Insecticidal activity of compounds of general formula I was assessed against the following pest:

*Trialeurodes vaporariorum* (greenhouse whitefly) (T.v.)

The test method employed appears below. In each test, solutions or suspensions of test compound were made up and sprayed as described above in Example 68.

French bean plants (*Phaseolus vulgaris*) with two fully expanded leaves were placed in a breeding culture of *T. vaporariorum*, also on French bean plants, which were then disturbed to ensure resettlement on the introduced plants. During the subsequent 24 hour period, eggs were deposited and kept at 27° C., with 14 hours photoperiod. All adult whiteflies were then carefully removed, leaving egg samples of a known age. After eight days the majority of eggs had hatched. Leaf discs containing the newly hatched nymphs were then cut from the leaves and transferred to moist filter paper. The discs were examined under a low-powered microscope to determine the exact number of 1st instar nymphs per disc and to remove any unhatched eggs. On average, 70–100 nymphs were found per disc. The discs were transferred into Petri dishes and sprayed with test solutions as described above. After 6 days percentage mortalities were assessed.

The $LC_{50}$ for each test compound was calculated as described above in Example 68. Ethyl parathion was used as the standard compound. The results are given in Table V below.

TABLE V

Insecticidal Activity

| Compound of Example No. | Toxicity Index T.v. |
|---|---|
| 5 | 320 |
| 22 | 180 |

TABLE V-continued

Insecticidal Activity

| Compound of Example No. | Toxicity Index T.v. |
| --- | --- |
| 27 | 95 |
| 36 | <20 |
| 37 | 190 |
| 39 | 95 |
| 45 | 370 |
| 48 | 17 |
| 49 | 27 |

EXAMPLE 71

Ectoparasiticidal Activity

In tests on tick larvae, *Boophilus decoloratus*, a concentration range of 1-25 ppm of the compound of Example 27 was used. Dead larvae were detected after 24 hours with all the concentrations, with the highest mortality occurring with the 25 ppm concentration. After 40 hours, no live larvae were observed with the 25 ppm concentration.

We claim:

1. A compound having the structural formula

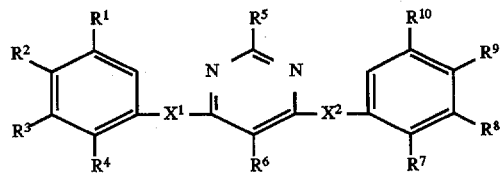

wherein $X^1$ and $X^2$ are the same and each represents an oxygen atom; a group $S(O)_n$ in which n is 0, 1 or 2; or a group CO, $CH_2$ or NR in which R represents a hydrogen atom or a $C_{1-6}$alkyl group;

$R^1$ and $R^{10}$ are the same or different and each represents a hydrogen atom or a halogen atom;

$R^2$ and $R^9$ are the same or different and each represents a hydrogen atom, a halogen atom or a cyano, nitro, $C_{1-6}$alkyl, halo$C_{1-6}$alkyl, $C_{1-6}$alkoxy, $C_{1-6}$alkylthio, amino, mono- or di($C_{1-6}$alkyl)amino, $C_{1-6}$alkoxy$C_{1-6}$alkyl, halo$C_{1-6}$alkoxy$C_{1-6}$alkyl or ($C_{1-6}$alkoxy) carbonyl group;

$R^3$ and $R^8$ are the same or different and each represents a hydrogen atom, a chlorine atom, or a $C_{1-6}$alkyl, halo$C_{1-6}$alkyl, halo$C_{1-6}$alkoxy, halo$C_{1-6}$alkylthio, halo$C_{2-6}$alkenyl, halo$C_{2-6}$alkynyl, halo$C_{1-6}$alkoxy$C_{1-6}$alkyl, (halo$C_{1-6}$alkoxy) carbonyl, halo$C_{1-6}$alkylsulphinyl, halo$C_{1-6}$alkylsulphonyl, nitro or cyano group;

$R^4$ and $R^7$ are the same or different and each represents a hydrogen atom, a halogen atom or a $C_{1-6}$alkyl or $C_{1-6}$alkoxy group;

$R^5$ represents a hydrogen atom, a halogen atom, or a cyano, $C_{1-6}$alkyl, halo$C_{1-6}$alkyl, $C_{1-6}$alkoxy, $C_{1-6}$alkylthio, $C_{1-6}$alkylsulphinyl or phenyl group; and $R^6$ represents a hydrogen atom or, when $R^5$ is hydrogen, a $C_{1-6}$alkyl group;

provided that at least one of $R^3$ and $R^8$ is other than hydrogen.

2. The compound according to claim 1 wherein each of $X^1$ and $X^2$ represents an oxygen atom, a sulphur atom or a group NH;

$R^1$ and $R^{10}$ are the same and each represents a hydrogen or a fluorine atom;

$R^2$ and $R^9$ are the same or different and each represents a hydrogen atom, a halogen atom, a nitro, $C_{1-4}$alkyl or cyano group;

$R^3$ and $R^8$ are the same or different and each represents a hydrogen, fluorine or chlorine atom, or a nitro, $C_{1-4}$alkyl, halo$C_{1-4}$alkyl, halo$C_{1-4}$alkoxy, halo$C_{2-4}$alkenyl or ($C_{1-4}$alkoxy) carbonyl group provided that at least one of $R^3$ and $R^8$ is a halo$C_{1-4}$alkyl group;

$R^4$ and $R^7$ are the same or different and each represents a hydrogen or halogen atom or a $C_{1-4}$alkyl group;

$R^5$ represents a hydrogen atom, a halogen atom or a halo$C_{1-4}$alkyl, $C_{1-4}$alkylthio or $C_{1-4}$alkylsulphinyl group; and $R^6$ represents a hydrogen atom or, when $R^5$ is hydrogen, a methyl group.

3. The compound according to claim 2, wherein each of $X^1$ and $X^2$ represents an oxygen atom; each of $R^1$ and $R^{10}$ represents a hydrogen atom; $R^2$ and $R^9$ are the same or different and each represents a hydrogen, fluorine or chlorine atom; $R^3$ and $R^8$ are the same or different and each represents a trifluoromethyl or pentafluoroethyl group; $R^5$ represents a hydrogen or chlorine atom, or a methylthio group; and $R^6$ represents a hydrogen atom.

4. The compound according to claim 3 selected from the group consisting of

4-[(4-chloro-α,α,α-trifluoro-m-tolyl)oxy]-6-[(α,α,α,4-tetra-fluoro-m-tolyl)oxy]pyrimidine;

4,6-bis[(4-chloro-α,α,α-trifluoro-m-tolyl)oxy]pyrimidine;

4,6-bis[(α,α,α,4-tetrafluoro-m-tolyl)oxy]-2-chloropyrimidine;

4,6-bis[(α,α,α,4-tetrafluoro-m-tolyl)oxy]-2-(methylthio)pyrimidine;

4-[(α,α,α,4-tetrafluoro-m-tolyl)oxy]-6-[(α,α,α-trifluoro-m-tolyl)oxy]pyrimidine;

4-[(4-chloro-α,α,α-trifluoro-m-tolyl)oxy]-6-[(α,α,α-trifluoro-m-tolyl)oxy]pyrimidine;

4,6-bis[(α,α,α,4-tetrafluoro-m-tolyl)oxy]pyrimidine; and 4,6-bis [m-(1,1,2,2,2-pentafluoroethyl)phenoxy]pyrimidine.

5. The compound according to claim 4 wherein the compound is 4-[(4-chloro-α,α,α-trifluoro-m-tolyl)oxy]-6-[(α,α,α,4-tetra-fluoro-m-tolyl)oxy]pyrimidine.

6. A method for controlling acarina and insects at a locus which method comprises applying to the locus an acaricidally or insecticidally effective amount of a compound having the structural formula

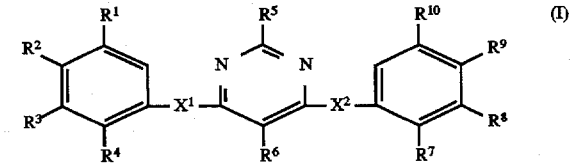

wherein $X^1$, $X^2$, $R^1$, $R^2$, $R^3$, $R^4$, $R^5$, $R^6$, $R^7$, $R^8$, $R^9$ and $R^{10}$ are as described in claim 1.

7. The method according to claim 6 wherein each of $X^1$ and $X^2$ represents an oxygen atom, a sulphur atom or a group NH;

$R^1$ and $R^{10}$ are the same and each represents a hydrogen or a fluorine atom;

$R^2$ and $R^9$ are the same or different and each represents a hydrogen atom, a halogen atom, a nitro, $C_{1-4}$alkyl or cyano group;

$R^3$ and $R^8$ are the same or different and each represents a hydrogen, fluorine or chlorine atom, or a nitro, $C_{1-4}$alkyl, halo$C_{1-4}$alkyl, halo$C_{1-4}$alkoxy, halo$C_{2-4}$alkenyl or ($C_{1-4}$alkoxy) carbonyl group provided that at least one of $R^3$ and $R^8$ is a halo$C_{1-4}$alkyl group;

$R^4$ and $R^7$ are the same or different and each represents a hydrogen or halogen atom or a $C_{1-4}$alkyl group;

$R^5$ represents a hydrogen atom, a halogen atom or a halo$C_{1-4}$alkyl, $C_{1-4}$alkylthio or $C_{1-4}$alkylsulphinyl group; and $R^6$ represents a hydrogen atom or, when $R^5$ is hydrogen, a methyl group.

8. The method according to claim 7 wherein each of $X^1$ and $X^2$ represents an oxygen atom;

each of $R^1$ and $R^{10}$ represents a hydrogen atom;

$R^2$ and $R^9$ are the same or different and each represents a hydrogen, fluorine or chlorine atom;

$R^3$ and $R^8$ are the same or different and each represents a trifluoromethyl or pentafluoroethyl group;

$R^5$ represents a hydrogen or chlorine atom, or a methylthio group; and $R^6$ represents a hydrogen atom.

9. The method according to claim 8 wherein the compound is selected from the group consisting of 4-[(4-chloro-α,α,α-trifluoro-m-tolyl)oxy]-6-[(α,α,α,4-tetra-fluoro-m-tolyl)oxy]pyrimidine;

4,6-bis[(4-chloro-α,α,α-trifluoro-m-tolyl)oxy] pyrimidine;

4,6-bis[(α,α,α,4-tetrafluoro-m-tolyl)oxy]-2-chloropyrimidine;

4,6-bis[(α,α,α,4-tetrafluoro-m-tolyl)oxy]-2-(methylthio) pyrimidine;

4-[(α,α,α,4-tetrafluoro-m-tolyl)oxy]-6-[(α,α,α-trifluoro-m-tolyl)oxy]pyrimidine;

4-[(4-chloro-α,α,α-trifluoro-m-tolyl)oxy]-6-[(α,α,α-trifluoro-m-tolyl)oxy]pyrimidine;

4,6-bis[(α,α,α,4-tetrafluoro-m-tolyl)oxy]pyrimidine; and 4,6-bis[m-(1,1,2,2,2-pentafluoroethyl)phenoxy] pyrimidine.

10. The method according to claim 6 wherein the acarina are mites.

11. A method for controlling animal ectoparasites which method comprises applying to the skin or coat of an animal an ectoparisiticidally effective amount of a compound having the structural formula

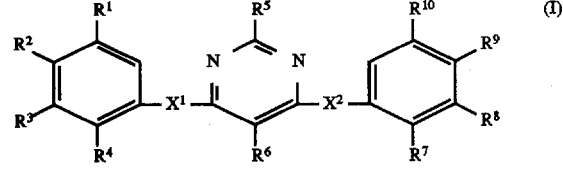

wherein $X^1$, $X^2$, $R^1$, $R^2$, $R^3$, $R^4$, $R^5$, $R^6$, $R^7$, $R^8$, $R^9$ and $R^{10}$ are as described in claim 1.

12. The method according to claim 11 wherein each of $X^1$ and $X^2$ represents an oxygen atom, a sulphur atom or a group NH;

$R^1$ and $R^{10}$ are the same and each represents a hydrogen or a fluorine atom;

$R^2$ and $R^9$ are the same or different and each represents a hydrogen atom, a halogen atom, a nitro, $C_{1-4}$alkyl or cyano group;

$R^3$ and $R^8$ are the same or different and each represents a hydrogen, fluorine or chlorine atom, or a nitro, $C_{1-4}$alkyl, halo$C_{1-4}$alkyl, halo$C_{1-4}$alkoxy, halo$C_{2-4}$alkenyl or ($C_{1-4}$alkoxy) carbonyl group provided that at least one of $R^3$ and $R^8$ is a halo$C_{1-4}$alkyl group;

$R^4$ and $R^7$ are the same or different and each represents a hydrogen or halogen atom or a $C_{1-4}$alkyl group;

$R^5$ represents a hydrogen atom, a halogen atom or a halo$C_{1-4}$alkyl, $C_{1-4}$alkylthio or $C_{1-4}$alkylsulphinyl group; and $R^6$ represents a hydrogen atom or, when $R^5$ is hydrogen, a methyl group.

13. The method according to claim 12 wherein each of $X^1$ and $X^2$ represents an oxygen atom;

each of $R^1$ and $R^{10}$ represents a hydrogen atom;

$R^2$ and $R^9$ are the same or different and each represents a hydrogen, fluorine or chlorine atom;

$R^3$ and $R^8$ are the same or different and each represents a trifluoromethyl or pentafluoroethyl group;

$R^5$ represents a hydrogen or chlorine atom, or a methylthio group; and $R^6$ represents a hydrogen atom.

14. The method according to claim 11 wherein the animal ectoparasites are ticks.

15. A composition for controlling acarina, insects and animal ectoparasites which composition comprises a carrier and an acaricidally, insecticidally or animal ectoparasiticidally effective amount of a compound having the structural formula

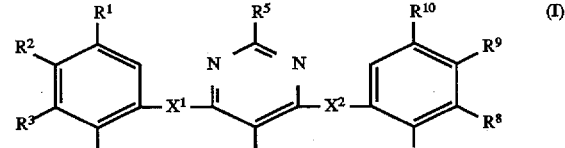

wherein $X^1$, $X^2$, $R^1$, $R^2$, $R^3$, $R^4$, $R^5$, $R^6$, $R^7$, $R^8$, $R^9$ and $R^{10}$ are as described in claim 1.

16. The composition according to claim 15 wherein each of $X^1$ and $X^2$ represents an oxygen atom, a sulphur atom or a group NH;

$R^1$ and $R^{10}$ are the same and each represents a hydrogen or a fluorine atom;

$R^2$ and $R^9$ are the same or different and each represents a hydrogen atom, a halogen atom, a nitro, $C_{1-4}$alkyl or cyano group;

$R^3$ and $R^8$ are the same or different and each represents a hydrogen, fluorine or chlorine atom, or a nitro, $C_{1-4}$alkyl, halo$C_{1-4}$alkyl, halo$C_{1-4}$alkoxy, halo$C_{2-4}$alkenyl or ($C_{1-4}$alkoxy) carbonyl group provided that at least one of $R^3$ and $R^8$ is a halo$C_{1-4}$alkyl group;

$R^4$ and $R^7$ are the same or different and each represents a hydrogen or halogen atom or a $C_{1-4}$alkyl group;

$R^5$ represents a hydrogen atom, a halogen atom or a halo$C_{1-4}$alkyl, $C_{1-4}$alkylthio or $C_{1-4}$alkylsulphinyl group; and $R^6$ represents a hydrogen atom or, when $R^5$ is hydrogen, a methyl group.

17. The composition according to claim 16 wherein
each of $X^1$ and $X^2$ represents an oxygen atom;
each of $R^1$ and $R^{10}$ represents a hydrogen atom;
$R^2$ and $R^9$ are the same or different and each represents a hydrogen, fluorine or chlorine atom;
$R^3$ and $R^8$ are the same or different and each represents a trifluoromethyl or pentafluoroethyl group;
$R^5$ represents a hydrogen or chlorine atom, or a methylthio group; and
$R^6$ represents a hydrogen atom.

18. The composition according to claim 17 wherein the compound is selected from the group consisting of 4-[(4-chloro-α,α,α-trifluoro-m-tolyl)oxy]-6-[(α,α,α,4-tetra-fluoro-m-tolyl)oxy]pyrimidine;

4,6-bis[(4-chloro-α,α,α-trifluoro-m-tolyl)oxy] pyrimidine;

4,6-bis[(α,α,α,4-tetrafluoro-m-tolyl)oxy]-2-chloropyrimidine;

4,6-bis[(α,α,α,4-tetrafluoro-m-tolyl)oxy]-2-(methylthio) pyrimidine;

4-[(α,α,α,4-tetrafluoro-m-tolyl)oxy]-6-[(α,α,α-trifluoro-m-tolyl)oxy]pyrimidine;

4-[(4-chloro-α,α,α-trifluoro-m-tolyl)oxy]-6-[(α,α,α-trifluoro-m-tolyl)oxy]pyrimidine;

4,6-bis[(α,α,α,4-tetrafluoro-m-tolyl)oxy]pyrimidine; and 4,6-bis[m-(1,1,2,2,2-pentafluoroethyl)phenoxy] pyrimidine.

19. A process for the preparation of a compound having the structural formula I as claimed in claim 1 in which $R^1=R^{10}$, $R^2=R^9$, $R^3=R^8$ and $R^4=R^7$, which process comprises reacting under basic conditions a 4,6-dihalopyrimidine compound having the structural formula

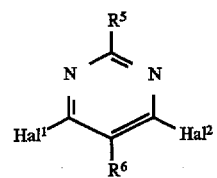

in which $R^5$ and $R^6$ are as defined in claim 1 and each of $Hal^1$ and $Hal^2$, independently, represents a halogen atom, with a compound having the structural formula

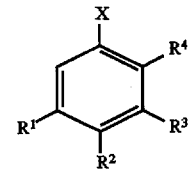

in which X represents a group $CH_2Hal$, COHal, OH, SH or NRH, Hal represents a halogen atom, and R, $R^1$, $R^2$, $R^3$ and $R^4$ are as defined in claim 1, in a molar ratio of at least 1:2.

20. An intermediate compound having the structural formula

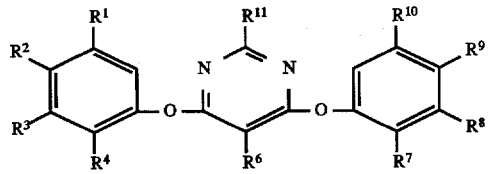

wherein $R^1$, $R^2$, $R^3$, $R^4$, $R^6$, $R^7$, $R^8$, $R^9$ and $R^{10}$ are as described in claim 1; and $R^{11}$ represents an OH or $NH_2$ group, provided that at least one of $R^3$ and $R^8$ is a halo$C_{1-6}$alkyl group.

* * * * *